US009629519B2

(12) United States Patent
Takazawa

(10) Patent No.: US 9,629,519 B2
(45) Date of Patent: Apr. 25, 2017

(54) ENDOSCOPE CONNECTION TOOL

(71) Applicant: OLYMPUS CORPORATION, Tokyo (JP)

(72) Inventor: Masataka Takazawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/008,534

(22) Filed: Jan. 28, 2016

(65) Prior Publication Data

US 2016/0135667 A1 May 19, 2016

Related U.S. Application Data

(63) Continuation of application No. PCT/JP2015/062253, filed on Apr. 22, 2015.

(30) Foreign Application Priority Data

May 13, 2014 (JP) ................................. 2014-099903

(51) Int. Cl.
| | |
|---|---|
| *A61B 1/00* | (2006.01) |
| *B08B 9/032* | (2006.01) |
| *A61B 1/12* | (2006.01) |

(52) U.S. Cl.
CPC ............ *A61B 1/00128* (2013.01); *A61B 1/12* (2013.01); *A61B 1/125* (2013.01); *B08B 9/032* (2013.01)

(58) Field of Classification Search
CPC .......... A61M 39/10; A61M 2039/1027; A61M 39/12; A61L 2/18; A61L 2/26;
(Continued)

(56) References Cited

U.S. PATENT DOCUMENTS 3,873,062 A  *  3/1975  Johnson ................... F16L 37/42
                                                    251/149.6
4,060,219 A  *  11/1977 Crawford ................ F16L 37/23
                                                    137/614.05
(Continued)

FOREIGN PATENT DOCUMENTS

| EP | 2 886 038 A1 | 6/2015 |
| JP | 5-317244 A | 12/1993 |

(Continued)

OTHER PUBLICATIONS

International Search Report dated Jul. 14, 2015 issued in PCT/JP2015/062253.
(Continued)

*Primary Examiner* — Michael Barr
*Assistant Examiner* — Benjamin L Osterhout
(74) *Attorney, Agent, or Firm* — Scully, Scott, Murphy & Presser, P.C.

(57) ABSTRACT

An endoscope connection tool includes a cylindrical portion having an inflow port connected to a fluid delivery apparatus, a discharge port discharging a fluid from the inflow port, and a flow path connecting the inflow port and the discharge port, a detection hole opened in an outer periphery of the cylindrical portion, and communicating with the flow path, a holding portion engaging with a pipe sleeve of an endoscope, and thereby holding the discharge port in a position facing an opening portion of the pipe sleeve, an urging member placed at the outer periphery of the cylindrical portion, and extending and contracting in a direction along the flow path, and a cover portion that is placed at the outer periphery of the cylindrical portion, moves to advance and retreat between a first position and a second position along the flow path by being interlocked with the urging member.

2 Claims, 12 Drawing Sheets

(58) Field of Classification Search
CPC ............ A61L 2202/123; A61L 2202/24; A61B 1/00128; A61B 1/12; A61B 1/125; B08B 9/032
See application file for complete search history.

(56) References Cited

U.S. PATENT DOCUMENTS

| | | | | |
|---|---|---|---|---|
| 4,188,942 | A * | 2/1980 | Fehlberg | A61B 1/00105 285/305 |
| 4,844,071 | A * | 7/1989 | Chen | A61B 1/042 600/112 |
| 4,920,961 | A * | 5/1990 | Grossi | A61B 1/00135 606/14 |
| 5,156,141 | A * | 10/1992 | Krebs | G02B 23/2476 600/112 |
| 6,354,521 | B1 * | 3/2002 | Kusilek | F16L 37/138 239/600 |
| 6,358,224 | B1 * | 3/2002 | Tims | A61M 1/0062 604/246 |
| 7,165,571 | B1 * | 1/2007 | Buzdum | F16L 41/02 137/112 |
| 8,622,893 | B2 * | 1/2014 | Mathieu | A61M 39/10 600/132 |
| 2009/0205687 | A1 | 8/2009 | Onishi et al. | |
| 2011/0232700 | A1 * | 9/2011 | Suzuki | A61L 2/18 134/198 |
| 2011/0298209 | A1 * | 12/2011 | Nguyen | A61M 39/10 285/321 |
| 2012/0007352 | A1 * | 1/2012 | Nguyen | A61M 39/12 285/84 |
| 2012/0031506 | A1 | 2/2012 | Komiya et al. | |

FOREIGN PATENT DOCUMENTS

| | | |
|---|---|---|
| JP | 2001-299697 A | 10/2001 |
| JP | 2004-135946 A | 5/2004 |
| JP | 2006-296857 A | 11/2006 |
| JP | 2010-99416 A | 5/2010 |

OTHER PUBLICATIONS

Extended Supplementary European Search Report dated Feb. 16, 2017 in related European Patent Application No. 15 79 3484.5.

* cited by examiner

ENDOSCOPE CONNECTION TOOL

CROSS REFERENCE TO RELATED APPLICATION

This application is a continuation application of PCT/JP2015/062253 filed on Apr. 22, 2015 and claims benefit of Japanese Application No. 2014-099903 filed in Japan on May 13, 2014, the entire contents of which are incorporated herein by this reference.

BACKGROUND OF THE INVENTION

1. Field of the Invention

The present invention relates to an endoscope connection tool that connects a fluid delivery apparatus and a pipe sleeve of an endoscope.

2. Description of the Related Art

Treatment using fluids such as cleaning treatment and disinfecting treatment is applied to endoscopes that are used in the medical field, after use. When the treatment using a fluid is performed for an endoscope having a conduit inside the endoscope, a fluid delivery apparatus that delivers the fluid, and a pipe sleeve that is provided at an end portion of the conduit are connected by an endoscope connection tool, and the fluid is caused to flow into the conduit.

The endoscope connection tool which connects a fluid delivery apparatus and a pipe sleeve of an endoscope like this is disclosed in Japanese Patent Application Laid-Open Publication No. 2001-299697, for example.

The fluid delivery apparatus disclosed in Japanese Patent Application Laid-Open Publication No. 2001-299697 has a flow rate measuring section that measures the flow rate of a fluid which is delivered to the endoscope connection tool, and has a configuration that notifies a user that a measurement result of the flow rate is outside a range of a set value when the measurement result of the flow rate is outside the range of the set value.

The conduit of an endoscope is elongated, and the flow resistance of the fluid is large. Consequently, a difference arises in the flow rate of the fluid which is delivered to the endoscope connection tool from the fluid delivery apparatus, between the case where the endoscope connection tool is correctly fitted to the pipe sleeve of the endoscope and the case where the endoscope connection tool is disengaged from the pipe sleeve. Accordingly, as in the art disclosed in Japanese Patent Laid-Open Publication No. 2001-299697, the flow rate of the fluid which is delivered to the endoscope connection tool is measured and is compared with the set value, whereby it can be determined whether or not the endoscope connection tool is correctly fitted to the pipe sleeve of the endoscope.

SUMMARY OF THE INVENTION

An endoscope connection tool according to one aspect of the present invention includes a cylindrical portion having an inflow port to which a fluid delivery apparatus is connected, a discharge port from which a fluid that flows in from the inflow port is discharged, and a flow path that connects the inflow port and the discharge port, a detection hole that is opened in an outer periphery of the cylindrical portion, and communicates with the flow path, a holding portion that engages with a pipe sleeve of an endoscope, and thereby holds the discharge port in a position facing an opening portion of the pipe sleeve, an urging member that is placed at the outer periphery of the cylindrical portion, and extends and contracts in a direction along the flow path, and a cover portion that is placed at the outer periphery of the cylindrical portion, moves to advance and retreat between a first position and a second position along the flow path by being interlocked with the urging member, is located in the first position that opens the detection hole by an urging force of the urging member when the holding portion does not engage with the pipe sleeve, and abuts on an outer surface of the endoscope to move to the second position which is nearer to the inflow port than the first position to close or narrow the detection hole when the holding portion engages with the pipe sleeve.

DETAILED DESCRIPTION OF THE PREFERRED EMBODIMENTS

Figure 1:
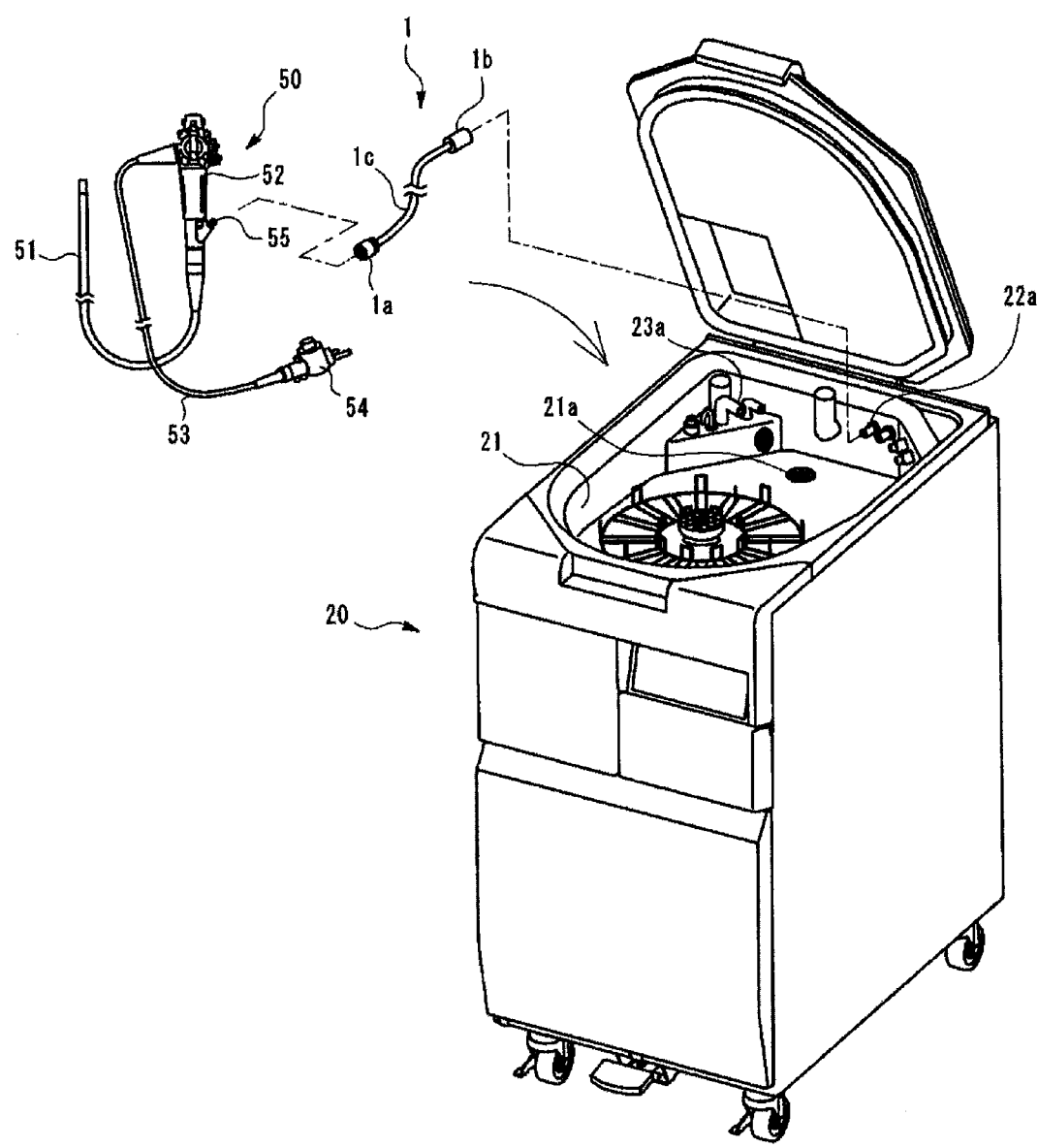
FIG. 1 is a perspective view of an endoscope, a fluid delivery apparatus and an endoscope connection tool.

Hereinafter, a preferable mode of the present invention will be described with reference to the drawings. Note that in respective drawings for use in the following explanation, a reduced scale is caused to differ at each of components, in order to illustrate the respective components to such an extent as to be recognizable on the drawings. The present invention is not limited only to the numbers and quantities of the components, shapes of the components, the ratios of the sizes of the components, relative positional relations of the respective components which are illustrated in the drawings.

As shown in FIG. 1, an endoscope connection tool 1 of the present embodiment is a device that connects a pipe sleeve 55 that is provided in an endoscope 50, and a fluid delivery apparatus 20. A configuration of the fluid delivery apparatus 20 is not specially limited as long as the fluid delivery apparatus 20 is an apparatus that delivers a fluid, and in the present embodiment, as one example, the fluid delivery apparatus 20 has a mode of an endoscope reprocessor.

First, a schematic configuration of the endoscope 50 will be described. Note that the endoscope 50 is well known, and therefore, explanation of the detailed configuration will be omitted.

As shown in FIG. 1 as one example, the endoscope 50 is configured mainly by including an insertion portion 51 that is introduced into a subject, an operation portion 52 that is provided at a proximal end side of the insertion portion 51, a universal cord 53 that is extended from the operation portion 52 and a connector portion 54 that is provided at the universal cord 53. The universal cord 53 and the connector portion 54 are components for connecting the endoscope 50 to outside apparatuses such as a light source apparatus and an image processing apparatus. The insertion portion 51 is provided with an objective lens for optically observing an inside of a subject, an illuminating light exit portion and the like.

Note that the subject to which the insertion portion 51 of the endoscope 50 is introduced is not limited to a human body, but may be another living body, or may be a structure such as a machine or a building. Further, the endoscope 50 may be in a mode that is described as a so-called flexible endoscope in which the insertion portion 51 is configured to be capable of bending as illustrated, or may be in a mode that is described as a so-called rigid endoscope in which the insertion portion 51 does not bend. Further, when the endoscope 50 has a mode that does not require electrical, optical or mechanical connection to outside apparatuses and is individually operable, the universal cord 53 and the connector portion 54 are not required.

Opening portions are provided in the operation portion 52 and the connector portion 54, for example, of the endoscope 50, and the pipe sleeves 55 are provided at the opening portions. The pipe sleeve 55 is provided to protrude from an outer surface of the endoscope 50. The pipe sleeves 55 are provided at an opening portion of a treatment instrument insertion channel that is provided in the operation portion 52, and an opening portion for a water leakage test that is provided in the connector portion 54, for example.

In the present embodiment, as one example, the pipe sleeve 55 is provided at the opening portion of the treatment instrument insertion channel which is provided in the operation portion 52. The treatment instrument insertion channel is a conduit in which one end is opened in the operation portion 52 and the other end is opened in a distal end portion of the insertion portion 51, and a treatment instrument can be inserted through an inside of the treatment instrument insertion channel.

Next, a schematic configuration of the fluid delivery apparatus 20 will be described with reference to FIG. 1 and FIG. 2. The fluid delivery apparatus 20 of the present embodiment has the mode of the endoscope reprocessor which carries out reprocessing treatment to the endoscope 50. The reprocessing treatment mentioned here is not specially limited, and may be any of rinsing by water, cleaning that eliminates contamination such as organic matters, disinfecting that makes predetermined microorganisms ineffective, sterilization that excludes or kills all microorganisms, and a combination of them.

The fluid delivery apparatus 20 includes a fluid delivery section 22 that is connected to the pipe sleeve 55 of the endoscope 50 via the endoscope connection tool 1. The fluid delivery section 22 is a part that delivers at least either one of gas and a liquid. Note that the fluid which is delivered by the fluid delivery section 22 is not limited to a case of only gas, and a case of only a liquid, but may be a gas-liquid two-phase fluid in which gas and a liquid are mixed.

The liquid delivery apparatus 20 of the present embodiment includes a treatment tank 21, a control section 24, a fluid supply section 23 and the fluid delivery section 22.

The treatment tank 21 is a vessel capable of accommodating the endoscope 50 in an inside. Note that in the drawing, the single endoscope 50 is accommodated in the treatment tank 21, but the treatment tank 21 may be configured to be able to accommodate the endoscopes 50 in plurality. In the treatment tank 21, a delivery port 22a of the fluid delivery section 22 and a supply port 23a of the fluid supply section 23 which will be described later are provided. Further, in the treatment tank 21, an intake port 21a is provided in a bottom surface or in a vicinity of the bottom surface.

The control section 24 is configured by including an arithmetic device (CPU), a storage device (RAM), an auxiliary storage device, an input/output device, an electric control device and the like, and has a configuration that controls operations of respective parts that configure the fluid delivery apparatus 20 based on a predetermined program.

The fluid supply section 23 includes a supply port 23a, an accumulation portion 23b and a pump 23c. The fluid supply section 23 discharges a liquid that is accumulated in the accumulation portion 23b into the treatment tank 21 from the supply port 23a by using the pump 23c. The liquid which is accumulated in the accumulation portion 23b is a cleaning liquid or a disinfecting liquid, for example. Note that the fluid supply section 23 may have a mode that switches and supplies a plurality of kinds of liquids such as water, alcohol, a cleaning liquid and a disinfecting liquid into the treatment tank 21.

The fluid delivery section 22 includes the delivery port 22a, a flow rate detection portion 22b and a pump 22c. In the present embodiment, as one example, the fluid delivery section 22 takes in the liquid which exists in the treatment tank 21 from the intake port 21a which is provided in the treatment tank 21, and delivers the liquid from the delivery port 22a by using the pump 22c.

The delivery port 22a is connected to the pipe sleeve 55 of the endoscope 50 via the endoscope connection tool 1 which will be described later. The fluid which is delivered from the delivery port 22a passes through the endoscope connection tool 1 and the pipe sleeve 55, and is introduced into the treatment instrument insertion channel. Since in the treatment instrument insertion channel, the other end is opened in the distal end portion of the insertion portion 51 as described above, the liquid which is introduced into the treatment instrument insertion channel returns into the treatment tank 21.

The flow rate detection portion 22b is a device that detects a flow rate of the fluid which is discharged from the delivery port 22a. The control section 24 recognizes the flow rate of the fluid which is discharged from the delivery port 22a, based on an output signal from the flow rate detection portion 22b.

The control section 24 determines that the endoscope connection tool 1 is detached from the pipe sleeve 55 when the flow rate of the fluid which is discharged from the delivery port 22a is larger than a threshold value that is set. Note that a mode in which a different value is used in accordance with a kind of the endoscope connection tool 1 as the threshold value may be adopted.

Further, in the delivery port 22a, a valve 22d that opens and closes the delivery port 22a is provided. The valve 22d brings the delivery port 22a into an open state when the endoscope connection tool 1 that will be described later is fitted to the delivery port 22a, and brings the delivery port into a closed state when the endoscope connection tool 1 is not fitted. Accordingly, when the fluid is not delivered from the delivery port 22a, the control section 24 determines that the endoscope connection tool 1 is detached from the delivery port 22a.

Note that a configuration of an endoscope reprocessor is well known, and therefore, detailed explanation of the configuration will be omitted.

Next, a configuration of the endoscope connection tool 1 will be described.

Figure 2:
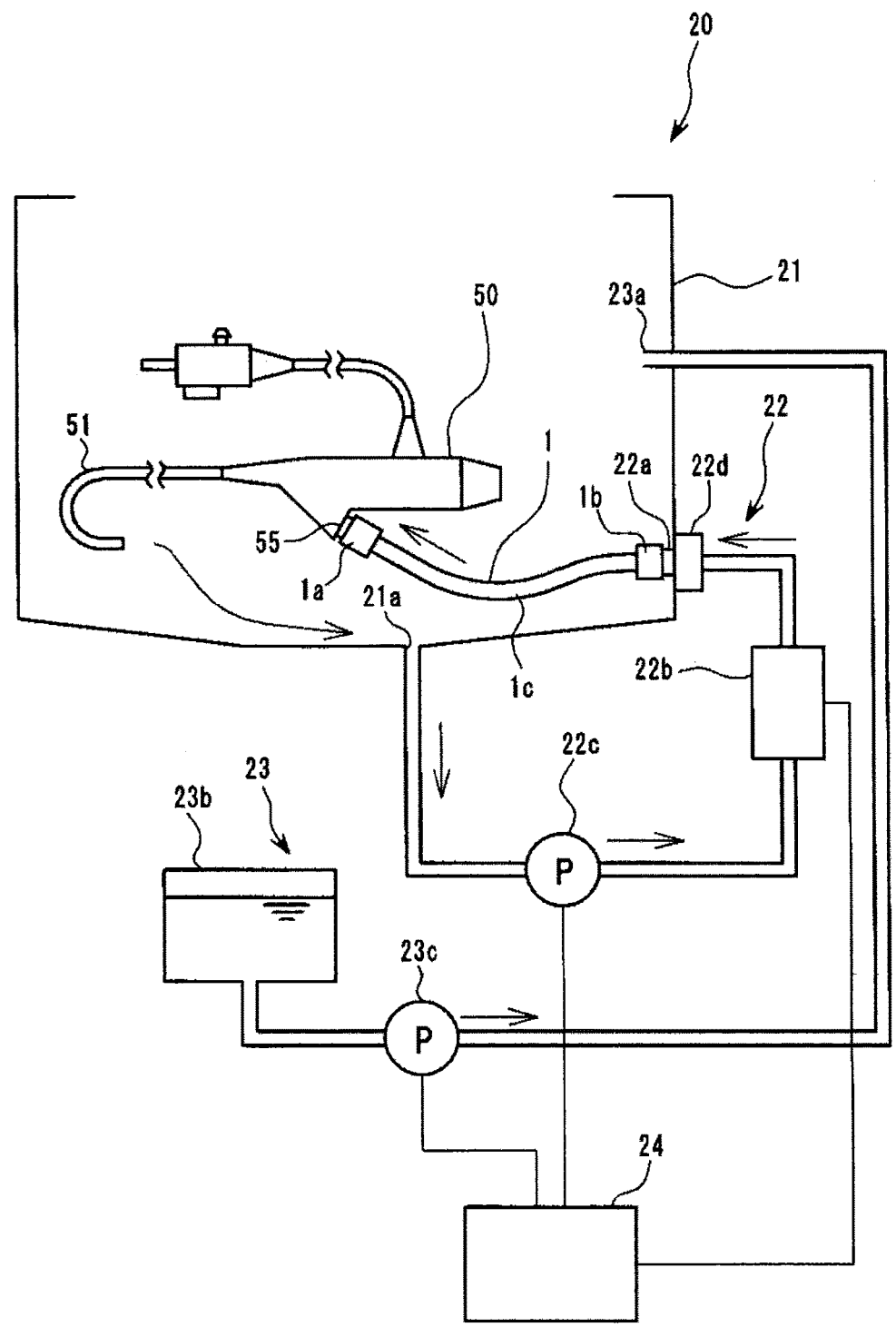
FIG. 2 is a view showing a configuration that connects the endoscope and the fluid delivery apparatus by the endoscope connection tool.

As shown in FIG. 1 and FIG. 2, the endoscope connection tool 1 of the present embodiment has a tube 1c, a pipe sleeve joint 1a that is provided at one end of the tube 1c, and a delivery port joint 1b that is provided at the other end of the tube 1c.

The pipe sleeve joint 1a is configured to connect an opening at one end side of the tube 1c to an opening that is provided in the pipe sleeve 55 by being fitted to the pipe sleeve 55 of the endoscope 50.

Further, the delivery port joint 1b is configured to connect an opening at the other end side of the tube 1c to the delivery port 22a by being fitted to the delivery port 22a of the fluid delivery apparatus 20. As described above, when the delivery port joint 1b is fitted to the delivery port 22a, the valve 22d which is provided at the delivery port 22a is brought into an open state.

The pipe sleeve joint 1a is fitted to the pipe sleeve 55, and the delivery port joint 1b is fitted to the delivery port 22a, whereby the pipe sleeve 55 and the delivery port 22a are connected via the endoscope connection tool 1, and the fluid which is delivered from the delivery port 22a is enabled to be introduced into the treatment instrument insertion channel.

Hereinafter, a configuration of the pipe sleeve joint 1a which is a part to be fitted to the pipe sleeve 55, of the endoscope connection tool 1 will be described.

Figure 3:
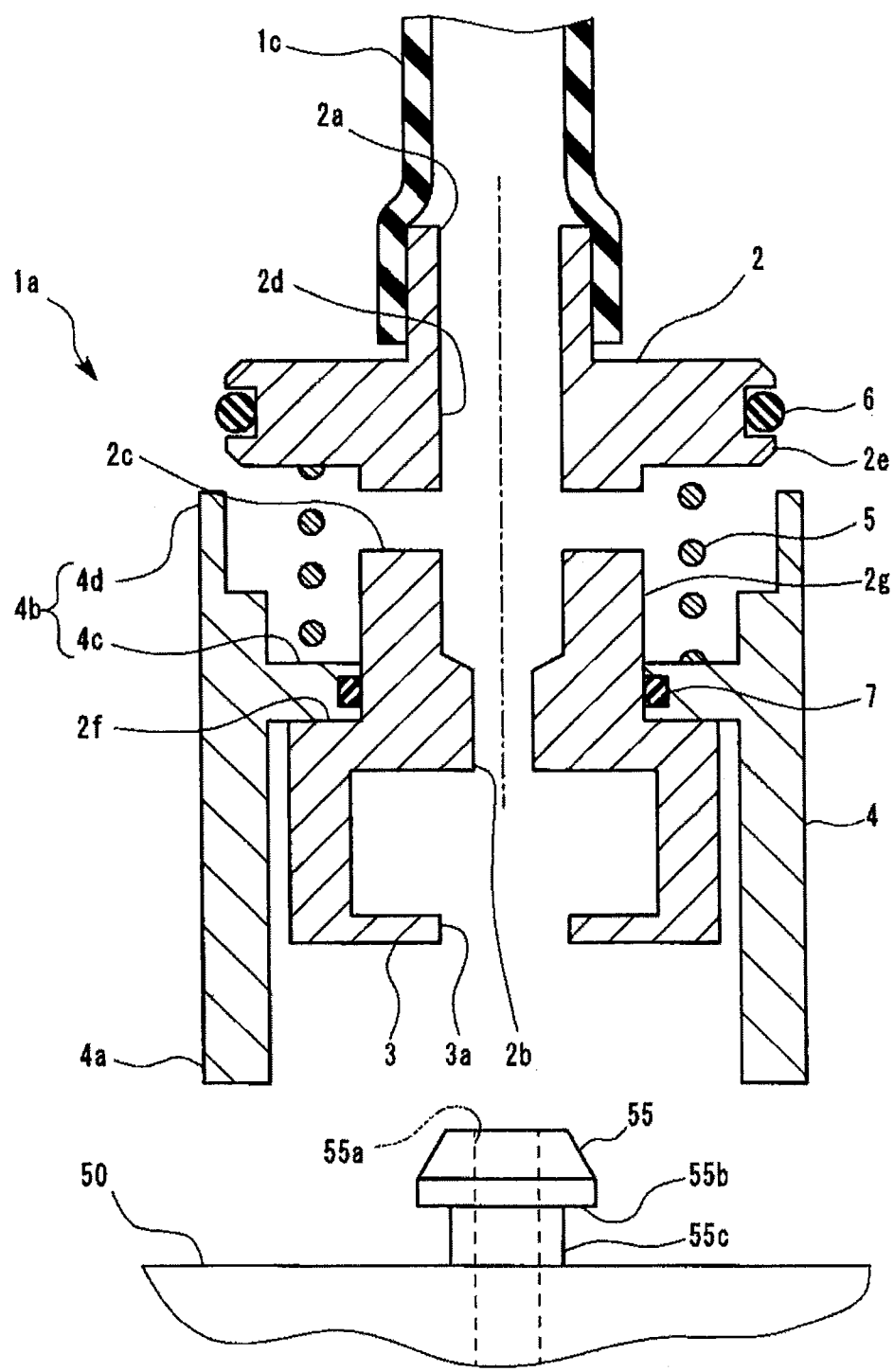
FIG. 3 is a sectional view of the endoscope connection tool of a first embodiment.
Figure 4:
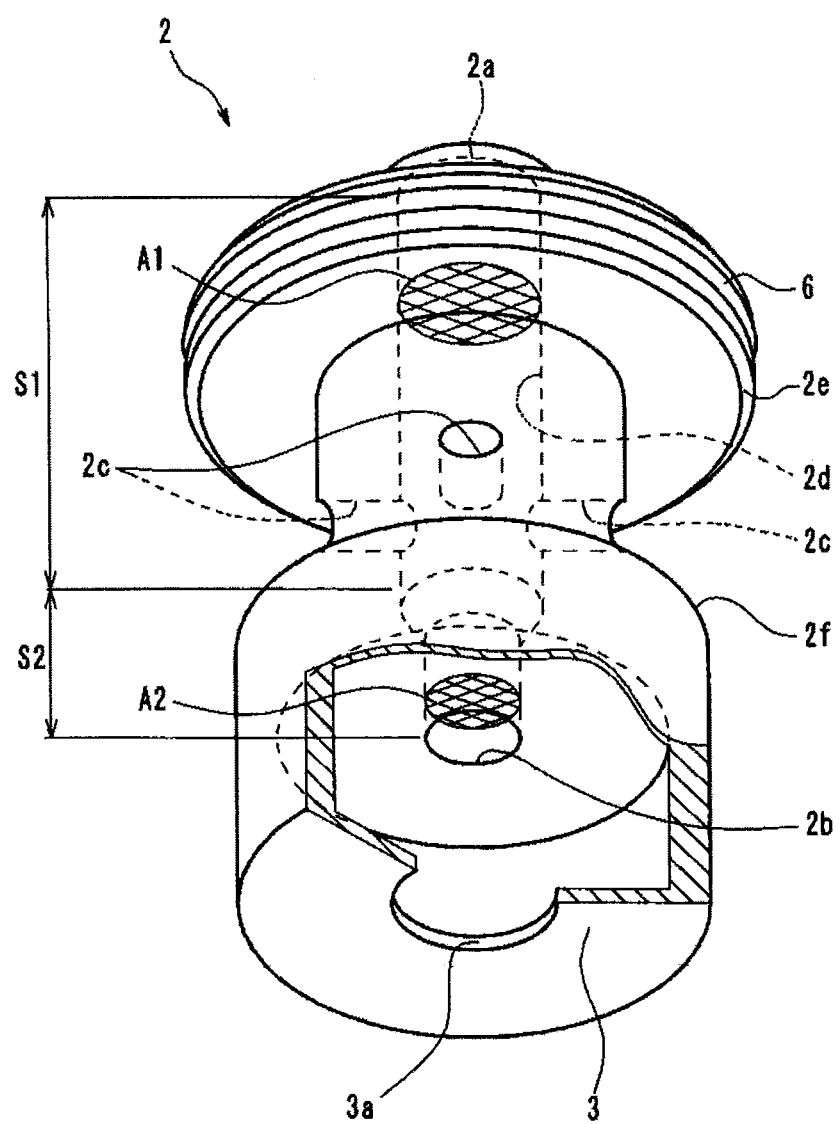
FIG. 4 is a perspective view of a cylindrical portion of the first embodiment.

As shown in FIG. 3 as a sectional view, the pipe sleeve joint 1a has a cylindrical portion 2, a holding portion 3, a cover portion 4 and an urging member 5.

The cylindrical portion 2 is a cylindrical member with both ends opened. At one end of the cylindrical portion 2, an inflow port 2a that is an opening portion is provided, and at the other end of the cylindrical portion 2, a discharge port 2b that is an opening portion is provided. Inside the cylindrical portion 2, a flow path 2d that causes the inflow port 2a and the discharge port 2b to communicate with each other is provided. That is, one end of the flow path 2d which penetrates through the cylindrical portion 2 is the inflow port 2a, and the other end is the discharge port 2b.

The tube 1c is connected to the inflow port 2a. That is, the inflow port 2a is connected to the fluid delivery apparatus 20 via the tube 1c. Accordingly, the fluid which is delivered from the fluid delivery apparatus 20 flows into the flow path 2d from the inflow port 2a. Subsequently, the fluid which flows into the flow path 2d is discharged from the discharge port 2b.

Further, in the cylindrical portion 2, a detection hole 2c is provided. The detection hole 2c is a through-hole that opens in an outer periphery of the cylindrical portion 2 and communicates with an inside of the flow path 2d. A detailed, configuration of the cylindrical portion 2 including the detection hole 2c will be described later.

The holding portion 3 is provided at an end portion where the discharge port 2b of the cylindrical portion 2 is provided. The holding portion 3 is configured to hold the discharge port 2b in a position facing an opening portion of the pipe sleeve 55 by engaging with the pipe sleeve 55. Note that the holding portion 3 may have a mode in which the holding portion 3 is provided integrally with the cylindrical portion 2 as illustrated, or may have a mode in which the holding portion 3 is a member different from the cylindrical portion 2 and is fixed to the cylindrical portion 2.

In the present embodiment, as one example, the pipe sleeve 55 is a cylindrical member that protrudes from the outer surface of the endoscope 50. An opening portion 55a that opens in the end portion of the pipe sleeve 55 which is cylindrical is an opening portion of the treatment instrument insertion channel in the present embodiment. At the end portion of the pipe sleeve 55, a flange portion 55b that protrudes more outward in a radial direction than a proximal portion 55c is formed.

The holding portion 3 engages with the flange portion 55b of the pipe sleeve 55. More specifically, the holding portion 3 is a plate-shaped member formed of a material that elastically deforms such as a rubber, and is provided with a through-hole 3a that has an inside diameter that is larger than the proximal portion 55c of the pipe sleeve 55, and is smaller than the flange portion 55b. The holding portion 3 is placed to be substantially orthogonal to an opening direction of the discharge port 2b, and the through-hole 3a is placed on a substantially same axis as the discharge port 2b.

Figure 5:
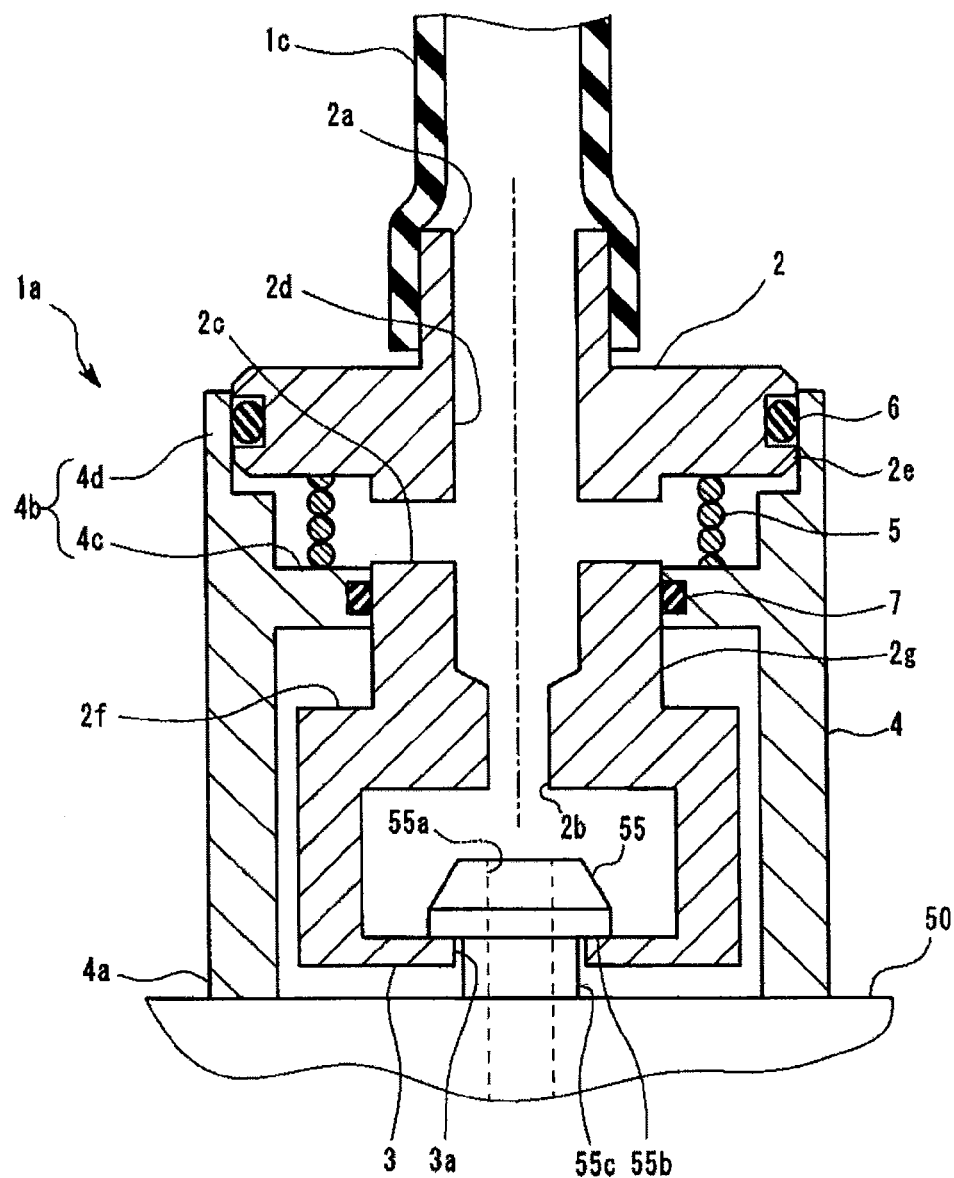
FIG. 5 is a sectional view of a state in which the endoscope connection tool of the first embodiment is fitted to a pipe sleeve.

Since an inside diameter of the through-hole 3a can be enlarged by elastic deformation of the holding portion 3, the flange portion 55b passes through the through-hole 3a by the pipe sleeve 55 being relatively forced into the through-hole 3a. In a state in which the flange portion 55b passes through the through-hole 3a, the opening portion 55a of the pipe sleeve 55 faces the discharge port 2b as shown in FIG. 5. Accordingly, the fluid which is discharged from the discharge port 2b is introduced into the opening portion 55a of the pipe sleeve 55.

The holding portion 3 engages with the pipe sleeve 55 as above, whereby the pipe sleeve joint 1a is fitted to the pipe sleeve 55. The pipe sleeve joint 1a is fitted to the pipe sleeve 55, whereby the delivery port 22a of the fluid delivery apparatus 20, and the opening portion 55a provided in the pipe sleeve 55 are connected by the endoscope connection tool 1.

Note that the holding portion 3 is not limited to a shape in the present embodiment. For example, the holding portion 3 may have a mode in which the holding portion 3 is configured by a plurality of claw-shaped (hook-shaped) members that extend inward in the radial direction, and the claw-shaped members are locked to the flange portion 55b.

Next, details of a configuration of the cylindrical portion 2 will be described.

The detection hole 2c which is provided in the cylindrical portion 2 is a through-hole in which one end is opened in an inner wall surface of the flow path 2d, and the other end is opened in an outer surface of the cylindrical portion 2. In the present embodiment, as one example, the detection hole 2c is opened in an outer periphery of a side surface of the cylindrical portion 2. A number of the detection holes 2c included by the cylindrical portion 2 may be one, or more than one. A sum total of sectional areas of the detection hole 2c is set as a third area A3.

Here, concerning the flow path 2d, in a case where a flow of the fluid that moves toward the discharge port 2b from the inflow port 2a in the flow path 2d is assumed, a direction toward the discharge port 2b from the inflow port 2a along the flow path 2d will be called a downstream direction, and a direction toward the inflow port 2a from the discharge port 2b will be called an upstream direction.

Concerning the flow path 2d, a zone from the inflow port 2a to the downstream direction, including a spot where the detection hole 2c is opened is set as a first zone S1, and a zone at a downstream side from the first zone S1 is set as a second zone S2. A part or all of the opening of the detection hole 2c is included in the first zone S1.

In the flow path 2d, in a case where a minimum sectional area in the first zone S1 is set as a first area A1, and a minimum sectional area in the second zone S2 is set as a second area A2, the second area A2 is smaller than the first area A1, as one example in the present embodiment. Note that the first area A1 does not include a sectional area of the detection hole 2c.

Note that the second area A2 may be a same as the first area A1, may be larger than the first area A1, or may be smaller than the first area A1. That is, the flow path 2d may be in a shape in which the sectional area does not change from the inflow port 2a to the discharge port 2b, may be in a shape in which the sectional area becomes larger toward the discharge port 2b from the inflow port 2a, or may be in a shape in which the sectional area becomes smaller toward the discharge port 2b from the inflow port 2a.

In the present embodiment, as one example, the cylindrical portion 2 is in a cylinder shape with a rectilinear axis as a center axis, and the flow path 2d is a rectilinear through-hole that penetrates through the cylindrical portion 2 with the center axis as a center. The flow path 2d is a circular hole having such an inside diameter that a sectional area becomes the first area A1 in the first zone S1. Further, the flow path 2d is a circular hole in the second zone S2, and a sectional area at a spot where inside diameter is the smallest is the second area A2.

The detection hole 2c is opened in an inner wall surface of the first zone S1 of the flow path 2d. Further, the detection hole 2c is opened in a side surface that is the outer surface of the cylindrical portion 2.

On the side surface of the cylindrical portion 2, a guide surface 2g on which the cover portion 4 which will be described later is slidably fitted is provided. The guide surface 2g is a cylinder surface having a same center axis as the cylindrical portion 2. The detection hole 2c is opened in the guide surface 2c of the side surface of the cylindrical portion 2.

A flange portion 2e and a stopper 2f that are protruded outward in the radial direction from the guide surface 2c are provided at an upstream side and a downstream side of the guide surface 2c. An outer circumferential face of the flange portion 2e is in a cylindrical shape.

The cover portion 4 is placed on the outer periphery of the cylindrical portion 2. The cover portion 4 is a member that moves to advance and retreat within a predetermined range in the flow direction of the flow path 2d along the outer surface of the cylindrical portion 2. In other words, the cover portion 4 moves in a direction toward the discharge port 2b from the inflow port 2a, and in a direction toward the inflow port 2a from the discharge port 2b, along the outer surface of the cylindrical portion 2. Here, an end at a downstream side in a range where the cover portion 4 moves to advance and retreat is called a first position.

The cover portion 4 is urged to a direction (the downstream side) toward the discharge port 2b from the inflow port 2a by the urging member 5 which is placed at the outer periphery of the cylindrical portion 2 and extends and contracts in a flow direction of the flow path 2d, such as a spring member. The cover portion 4 is disposed in the first position by an urging force of the urging member 5 when the cover portion 4 does not contact a matter other than the component members of the pipe sleeve joint 1a. When a force in the upstream direction is applied with respect to the flow direction of the flow path 2d, the cover portion 4 moves in the upstream direction.

The cover portion 4 has a protruded portion 4a and a lid portion 4b.

The protruded portion 4a is a part that protrudes in an opening direction of the discharge port 2b from the discharge port 2b, when the cover portion 4 is located in the first position. The protruded portion 4a abuts on the outer surface of the endoscope 50 in a vicinity of the pipe sleeve 55 in a state where the holding portion 3 engages with the pipe sleeve 55. In the state where the holding portion 3 engages with the pipe sleeve 55, the protruded portion 4a abuts on the outer surface of the endoscope 50, whereby the cover portion 4 moves in the upstream direction from the first position, and is located in a second position.

Note that the second position does not have to be an end portion at an upstream side of a range of relative movement of the cover portion 4 to the cylindrical portion 2. That is, the cover portion 4 may be movable to the upstream side from the second position.

The lid portion 4b is a part that closes the detection hole 2c, or decreases an opening area of the detection hole 2c, when the cover portion 4 is located in the second position.

FIG. 3 shows a state where the cover portion 4 is located in the first position. Further, FIG. 5 shows a state where the holding portion 3 engages with the pipe sleeve 55, and the cover portion 4 is located in the second position.

In the present embodiment, as one example, the cover portion 4 is a member in a cylindrical shape which is concentric with the cylindrical portion 2, and the cylindrical portion 2 is inserted to an inside of the cover portion 4. The cover portion 4 has a slide portion 4c having such an inside diameter as to be fitted onto a periphery of the guide surface 2g of the cylindrical portion 2. The slide portion 4c is a part that protrudes inward in the radial direction from an inner circumferential face of the cover portion 4. The slide portion 4c is fitted onto the periphery of the guide surface 2g of the cylindrical portion 2, whereby the cover portion 4 moves to advance and retreat relatively to the cylindrical portion 2 substantially parallel with the center axis of the cylindrical portion 2. A position in which the slide portion 4c abuts on the stopper 2f is the end at the downstream side of the range of the relative movement of the cover portion 4 to the cylindrical portion 2, and is the first position.

The slide portion 4c is fitted onto the guide surface 2g at the downstream side from the detection hole 2c. That is, in the present embodiment, the slide portion 4c is always fitted to the guide surface 2g at the downstream side from the detection hole 2c, irrespective of the relative position of the cover portion 4 to the cylindrical portion 2.

The urging member 5 is a compression coil spring that is wound around the periphery of the guide surface 2g of the cylindrical portion 2. The urging member 5 is sandwiched between the flange portion 2e which is provided to protrude outward in the radial direction from the outer periphery of the cylindrical portion 2, and the slide portion 4c which is provided to protrude inward in the radial direction from an inner periphery of the cover portion 4.

Accordingly, the cover portion 4 is urged in a direction to move toward the downstream side relatively to the cylindrical portion 2, by the urging member 5. When the cover portion 4 does not contact a matter other than the component members of the pipe sleeve joint 1a, the cover portion 4 is located in the first position in which the slide portion 4c is butted to the stopper 2f, as shown in FIG. 3.

The lid portion 4b is configured by an upstream side end portion 4d and the slide portion 4c of the cover portion 4. The upstream side end portion 4d is a cylindrical part having such an inside diameter as to be fitted on an outer periphery of the flange portion 2e of the cylindrical portion 2 when the cover portion 4 is located in the second position as shown in FIG. 5. The upstream side end portion 4d is apart from the flange portion 2e when the cover portion 4 is located at the downstream side from the second position, as shown in FIG. 3.

When the cover portion 4 is located in the second position, the opening portion at an outer side of the detection hole 2c is surrounded by the flange portion 2e, the upstream side end portion 4d and the slide portion 4c. That is, when the cover portion 4 is located in the second position, the detection hole 2c is closed by the lid portion 4b. Further, when the cover portion 4 is located at the downstream side from the second position, the opening portion at the outer side of the detection hole 2c is opened toward an external space of the pipe sleeve joint 1a.

Note that in the present embodiment which is illustrated, as one example, seal portions 6 and 7 are placed, which are members that enhance sealing performance of closure of the detection hole 2c by the lid portion 4c by being interposed between the cylindrical portion 2 and the lid portion 4c. The seal portion 6 is fitted into a groove which is provided by being engraved in a circumferential direction on an outer circumferential face of the flange portion 2e, and the seal portion 7 is fitted into a groove that is provided by being engraved in a circumferential direction on an inner circumferential face of the slide portion 4c. In the present embodiment which is illustrated, the seal portions 6 and 7 are so-called O-shaped rings that are circular in sections, but the seal portions 6 and 7 may be X-shaped or rectangular in sections, for example. Note that when sufficient sealing performance in the case of the detection hole 2c being closed is obtained by the fitting shape of the cylindrical portion 2 and the lid portion 4c, the seal portions 6 and 7 are not required.

The protruded portion 4a is a downstream side end portion of the cover portion 4 which is in the cylindrical shape, and in the state where the cover portion 4 is located in the first position as shown in FIG. 3, the protruded portion 4a protrudes in the opening direction of the discharge port 2b from the discharge port 2b and the holding portion 3. Here, the opening direction of the discharge port 2b is a same as the downstream direction of the flow path 2d in the present embodiment.

Since the protruded portion 4a protrudes more to the downstream side than the holding portion 3, the protruded portion 4a abuts on the outer surface of the endoscope 50 earlier than the holding portion 3 when the pipe sleeve joint 1a is fitted to the pipe sleeve 55. As described above, when the pipe sleeve joint 1a is to be fitted to the pipe sleeve 55 in the present embodiment, the holding portion 3 engages with the pipe sleeve 55 by performing an operation of relatively pressing the pipe sleeve 55 into the through-hole 3a of the holding portion 3. In the operation, the protruded portion 4a abuts on the outer surface of the endoscope 50 before the holding portion 3 engages with the pipe sleeve 55.

Accordingly, when the holding portion 3 engages with the pipe sleeve 55, the protruded portion 4a abuts on the outer surface of the endoscope 50, whereby the cover portion 4 moves to the upstream side relatively to the cylindrical portion 2. In the state where the holding portion 3 engages with the pipe sleeve 55, the protruded portion 4a abuts on the outer surface of the endoscope 50, whereby the cover portion 4 is located in the second position, as shown in FIG. 5.

As described above, in the endoscope connection tool 1 of the present embodiment, the cover portion 4 closes the detection hole 2c provided in the cylindrical portion 2 when the pipe sleeve joint 1a is correctly fitted to the pipe sleeve 55, whereas the cover portion 4 opens the detection hole 2c when the pipe sleeve joint 1a is not fitted to the pipe sleeve 55.

Accordingly, when the pipe sleeve joint 1a is correctly fitted to the pipe sleeve 55, the detection hole 2c is closed, and therefore the fluid which is delivered from the fluid delivery apparatus 20 and flows into the endoscope connection tool 1 flows outside the endoscope connection tool 1 only through the discharge port 2b. In other words, when the pipe sleeve joint 1a is correctly fitted to the pipe sleeve 55, the fluid which is delivered from the fluid delivery apparatus 20 and flows into the endoscope connection tool 1 passes through only the second zone S2 in which the minimum sectional area is the second area A2, and flows outside the endoscope connection tool 1.

When the pipe sleeve joint 1a is correctly fitted to the pipe sleeve 55, the discharge port 2b faces the opening portion 55a of the pipe sleeve 55, and therefore, a flow rate Q1 of the fluid which flows out from the endoscope connection tool 1 is determined by either the second area A2 or flow resistance in the conduit which connects to the opening portion 55a.

When the pipe sleeve joint 1a is not fitted to the pipe sleeve 55, the detection hole 2c is opened, and therefore, the fluid which is delivered from the fluid delivery apparatus 20 and flows into the endoscope connection tool 1 passes through the discharge port 2b and the detection hole 2c and flows outside the endoscope connection tool 1. In other words, the fluid which is delivered from the fluid delivery apparatus 20 and flows into the endoscope connection tool 1 passes through the detection hole 2c having the third area A3 in addition to the second zone S2 in which the minimum sectional area is the second area A2 and flows outside the endoscope connection tool 1, when the pipe sleeve joint 1a is not fitted to the pipe sleeve 55.

That is, when the pipe sleeve joint 1a is not fitted to the pipe sleeve 55, a flow rate Q2 of the fluid which flows out from the endoscope connection tool 1 includes a flow rate of the fluid flowing out from the detection hole 2c, and therefore is clearly larger as compared with the flow rate Q1 in the case where the pipe sleeve joint 1a is correctly fitted to the pipe sleeve 55.

Accordingly, the endoscope connection tool 1 of the present embodiment can clarify the difference of the flow rates of the fluid which differ depending on presence and absence of fitting to the pipe sleeve 55 of the endoscope 50.

Further, the flow rate of the fluid which flows out from the endoscope connection tool 1 in the case where the pipe sleeve joint 1a is not fitted to the pipe sleeve 55 is determined by the first area A1, the second area A2 and the third area A3 which have known values. Accordingly, a difference between the flow rate Q2 and the flow rate Q1 is a value that can be obtained in advance.

Consequently, in the fluid delivery apparatus 20, setting of the threshold value for the control section 24 to determine whether or not the endoscope connection tool 1 is detached from the pipe sleeve 55 based on the flow rate of the fluid which is discharged from the delivery port 22a is facilitated.

For example, if an RFID tag including information expressing the first area A1, the second area A2 and the third area A3 of the endoscope connection tool 1 is attached to the endoscope connection tool 1, and the fluid delivery apparatus 20 is provided with a device that reads the RFID tag, the control section 24 of the fluid delivery apparatus 20 can automatically calculate the threshold value of the flow rate for determining whether or not the endoscope connection tool 1 is detached from the pipe sleeve 55 based on the information which is read from the RFID tag.

Note that in this case, the information contained by the RFID tag does not have to be the information expressing the first area A1, the second area A2 and the third area A3, but can be information that allows the control section 24 to set the threshold value based on the information. For example, the information contained by the RFID tag may express the threshold value itself, or may express a model number of the endoscope connection tool 1.

Note that in the above explanation, the second area A2 of the flow path 2d of the cylindrical portion 2 is described as smaller than the first area A1, as one example, but even in the case where the second area A2 is a same as the first area A1 or larger than the first area A1, the point that a change occurs to the flow rate of the fluid which flows out from the endoscope connection tool 1 in accordance with opening or closing the detection hole 2c is similar to the above explanation. Accordingly, even when the second area A2 of the flow path 2d is the same as the first area A1 or larger than the first area A1, the endoscope connection tool 1 can clarify the difference in the flow rate of the fluid which differs depending on the presence or absence of fitting to the pipe sleeve 55 of the endoscope 50.

The present embodiment described above has the configuration in which the cylindrical upstream side end portion 4b is fitted onto the outer periphery of the flange portion 2e and closes or narrows the detection hole 2c, in the state where the cover portion 4 is located in the second position. However, the configuration in which the cover portion 4 closes or narrows the detection hole 2c in the state where the cover portion 4 is located in the second position is not limited to the present embodiment.

Figure 6:
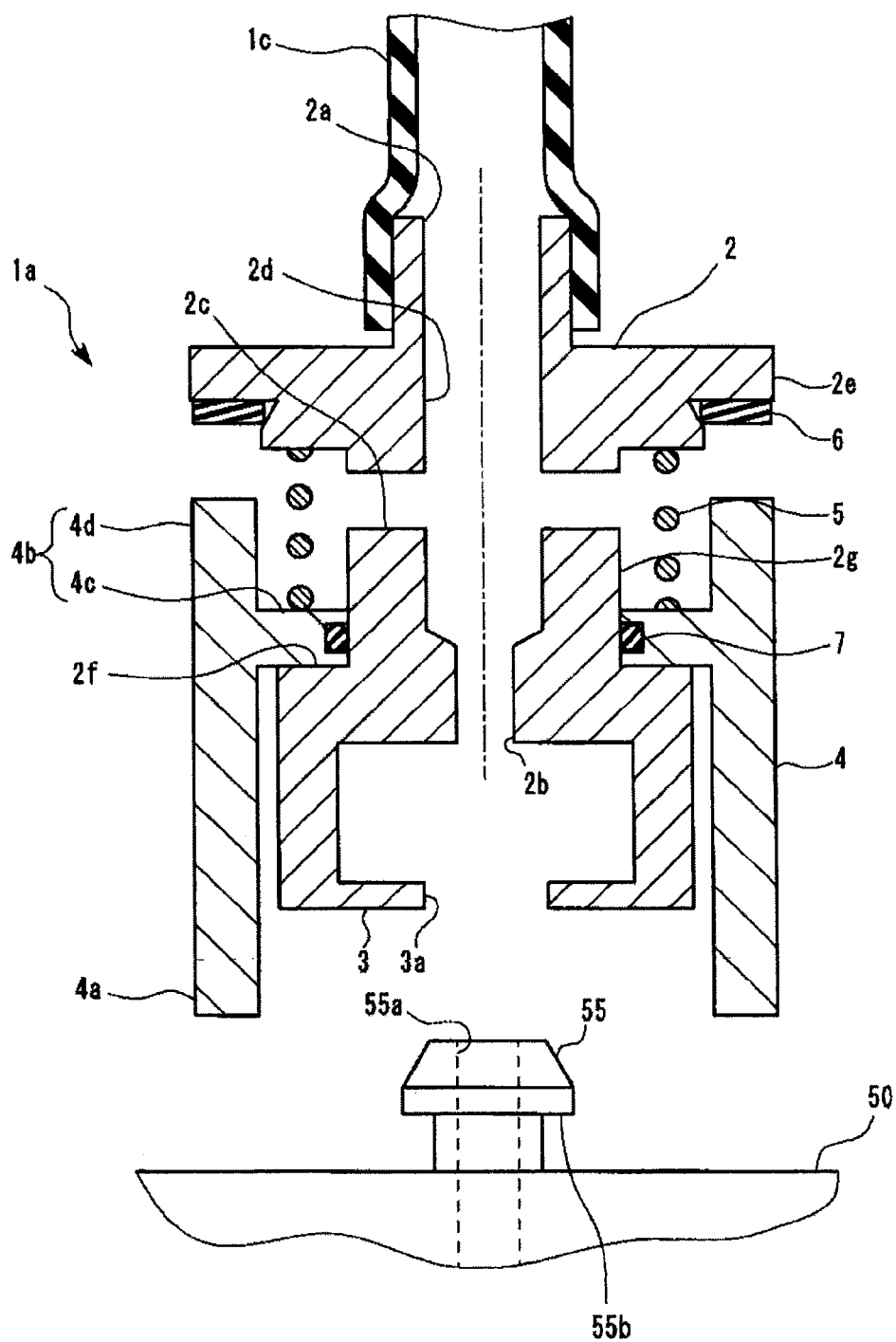
FIG. 6 is a sectional view of an endoscope connection tool of a first modification example of the first embodiment.
Figure 7:
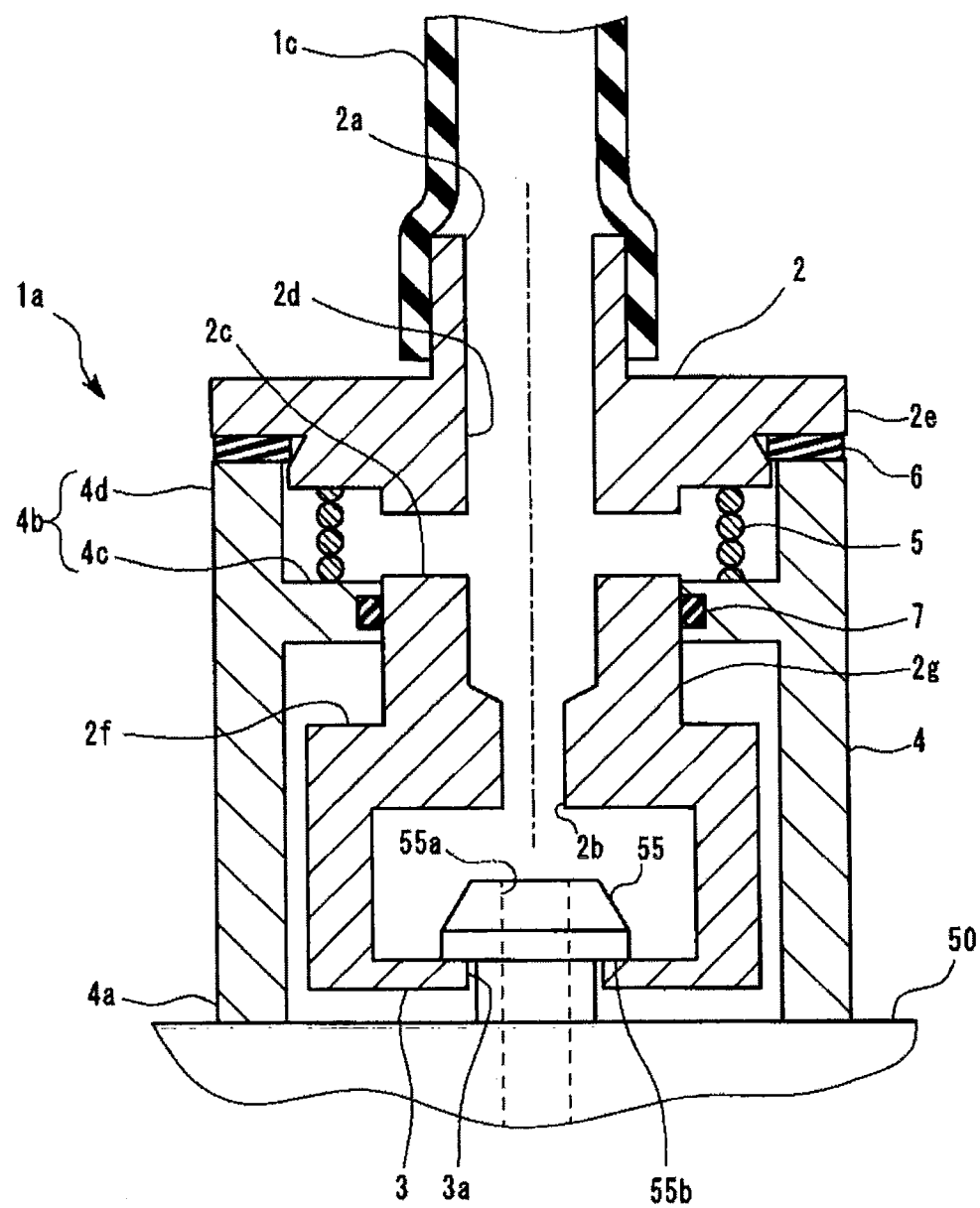
FIG. 7 is a sectional view of a state in which the endoscope connection tool of the first modification example of the first embodiment is fitted to a pipe sleeve.

For example, as shown in FIG. 6 and FIG. 7 as a first modification example, a configuration may be adopted, in which in the state where the cover portion 4 is located in the second position, an end surface of the cylindrical upstream side end portion 4b is butted to an end surface at the downstream side of the flange portion 2e, and thereby closes or narrows the detection hole 2c. When the cover portion 4 is located at a downstream side from the second position, the end surface of the upstream side end portion 4b and the end surface at the downstream side of the flange portion 2e are apart from each other, and the detection hole 2c is opened to outside as shown in FIG. 6.

Further, in the first modification example, in the state where the cover portion 4 is located in the second position, a seal portion 6 that is a packing is sandwiched between the upstream side end portion 4b and the flange portion 2e. The seal portion 6 is fixed to the downstream side end surface of the flange portion 2e as shown in FIG. 6.

Figure 8:
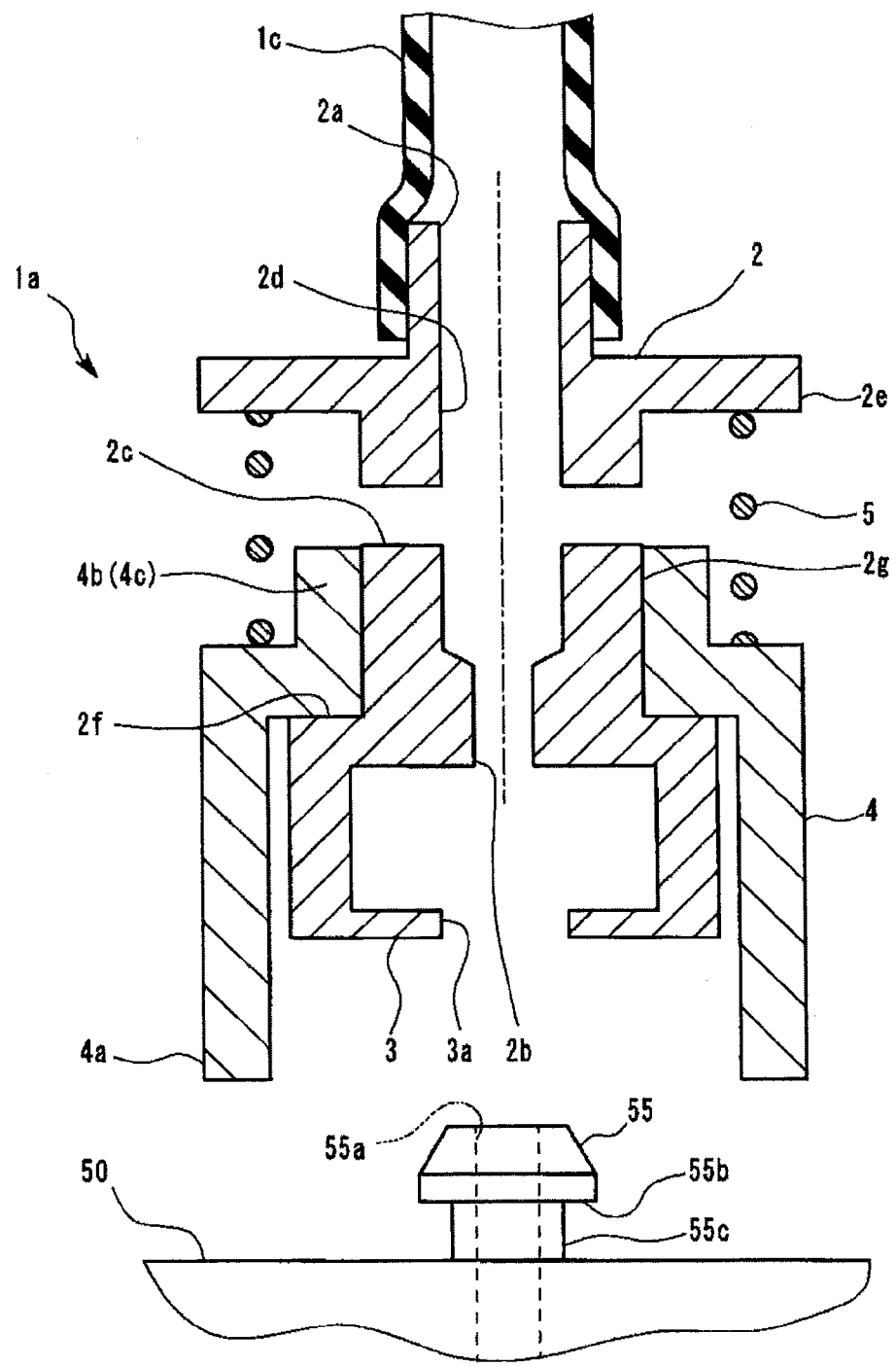
FIG. 8 is a sectional view of an endoscope connection tool of a second modification example of the first embodiment.
Figure 9:
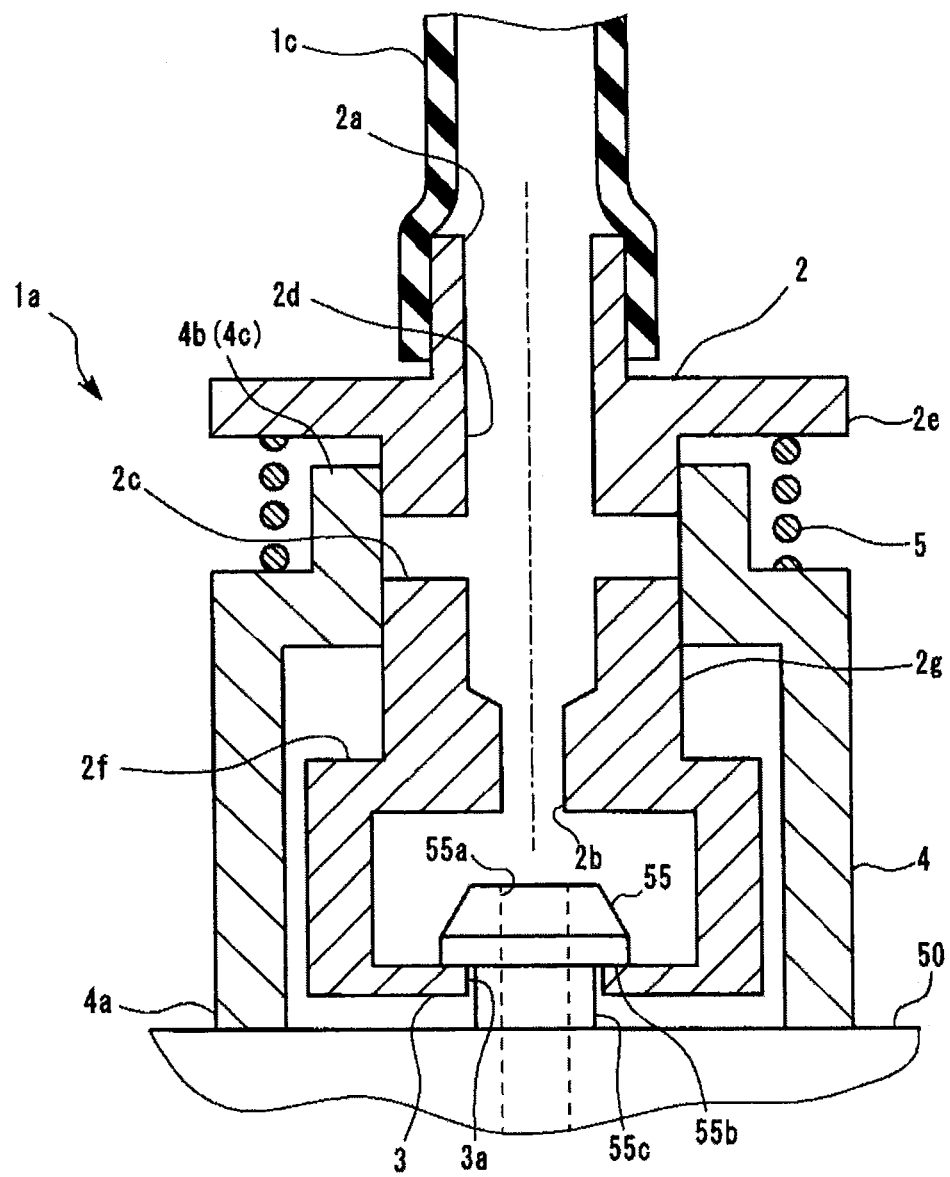
FIG. 9 is a sectional view of a state in which the endoscope connection tool of the second modification example of the first embodiment is fitted to a pipe sleeve.

Further, for example, as shown in FIG. 8 and FIG. 9 as a second modification example, a configuration may be adopted, in which in the state where the cover portion 4 is located in the second position, the detection hole 2c is covered by the slide portion 4c of the cover portion 4, and thereby the detection hole 2c is closed or narrowed. When the cover portion 4 is located in the first position, the slide portion 4c retreats from the opening portion of the detection hole 2c, and the detection hole 2c is opened to outside.

The endoscope connection tools 1 of the first and second modification examples can also clarify the fluid rate difference of the fluid which differs depending on presence or absence of fitting to the pipe sleeve 55 of the endoscope 50 as described above.

Second Embodiment

Next, a second embodiment of the present invention will be described. Hereinafter, only a difference from the first embodiment will be described, components similar to those in the first embodiment are assigned with the same reference signs and explanation of them will be properly omitted.

Figure 10:
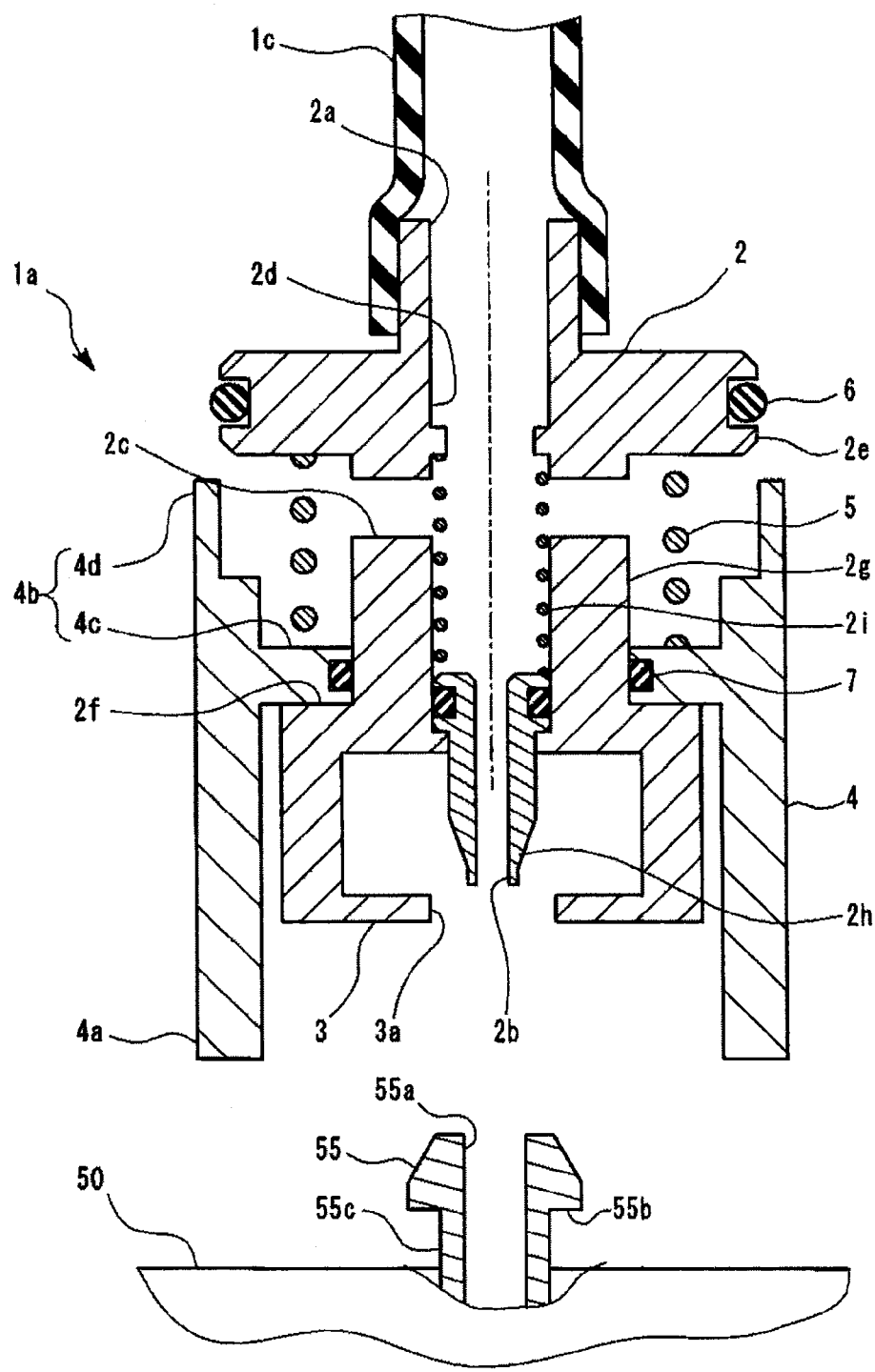
FIG. 10 is a sectional view of an endoscope connection tool of a second embodiment.
Figure 11:
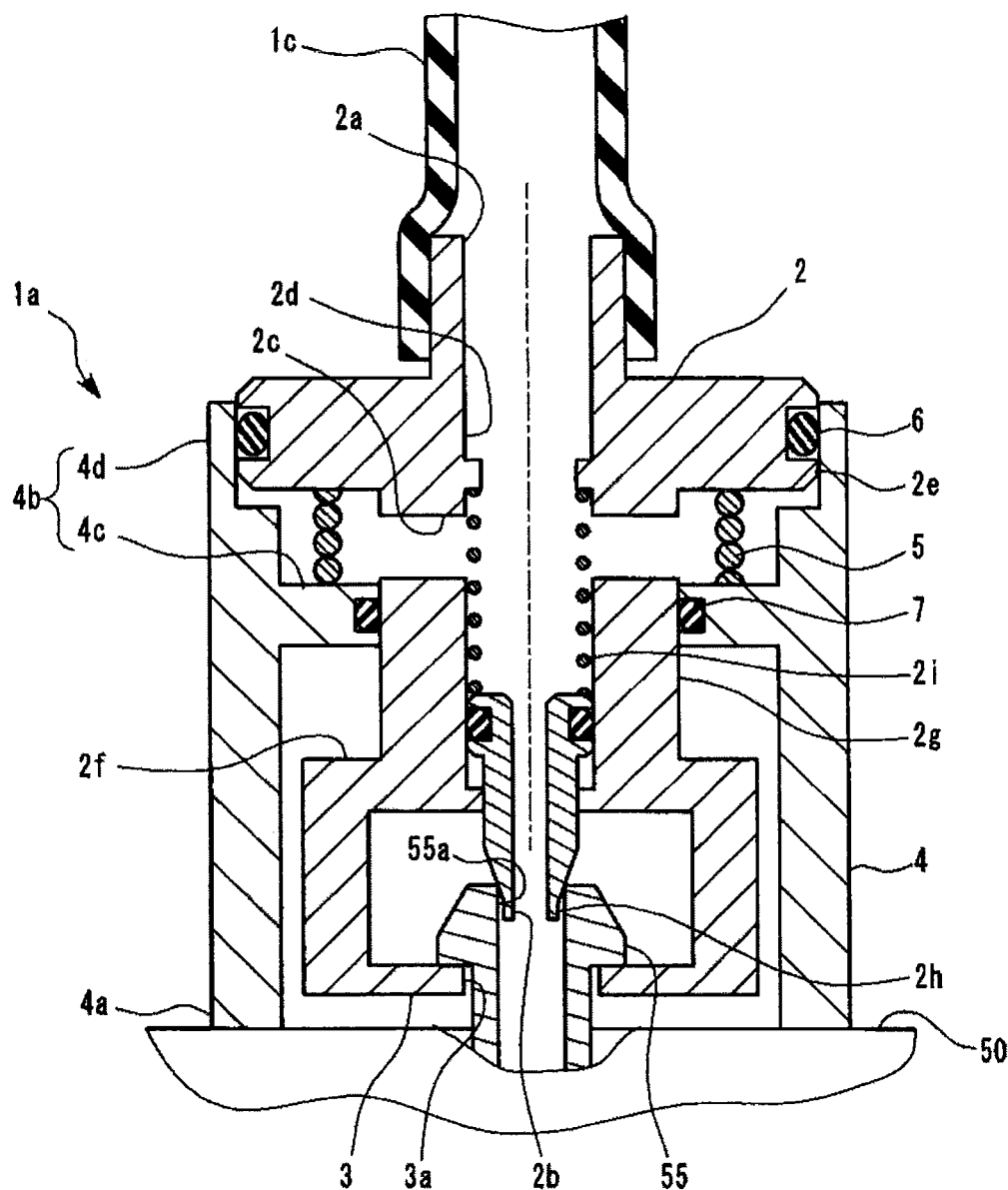
FIG. 11 is a sectional view of a state in which the endoscope connection tool of the second embodiment is fitted to a pipe sleeve.

FIG. 10 and FIG. 11 are sectional views of the pipe sleeve joint 1a of the endoscope connection tool 1 of the present embodiment. As shown in FIG. 11, the pipe sleeve joint 1a of the present embodiment has a discharge nozzle 2h that is inserted into the opening portion 55a in the pipe sleeve 55 in a state in which the pipe sleeve joint 1a is fitted to the pipe sleeve 55 of the endoscope 50.

The discharge nozzle 2h is placed at the downstream side end portion of the cylindrical portion 2, and is inserted into the opening portion 55a in a state where the holding portion 3 engages with the pipe sleeve 55. The discharge port 2b of the cylindrical portion 2 of the present embodiment is provided at a downstream side end portion of the discharge nozzle 2h. Consequently, a flow rate of the fluid which is discharged from the discharge port 2b, and enters the opening portion 55a can be stabilized.

In the present embodiment, the discharge nozzle 2h is placed so as to move to advance and retreat along the center axis of the flow path 2d. The discharge nozzle 2h is urged toward the downstream side by the urging member 2i. That is, the discharge nozzle 2h can be pushed in toward the upstream side. As shown in FIG. 11, the discharge nozzle 2h is disposed to be slightly pushed to the upstream side, in the state where the holding portion 3 engages with the pipe sleeve 55.

The discharge nozzle 2h which is provided with the discharge port 2b is placed to move to advance and retreat along the center axis of the flow path 2d like this, whereby the position of the discharge port 2b in the opening portion 55a can be fixed irrespective of variations of sizes of the holding portion 3 and the pipe sleeve 55. Accordingly, the flow rate of the fluid which is discharged from the discharge port 2b and enters the opening portion 55a can be stabilized.

Third Embodiment

Next, a third embodiment of the present invention will be described. Hereinafter, only a difference from the first embodiment and the second embodiment will be described, components similar to those in the first embodiment and the second embodiment are assigned with the same reference signs and explanation of them will be properly omitted.

Figure 12:
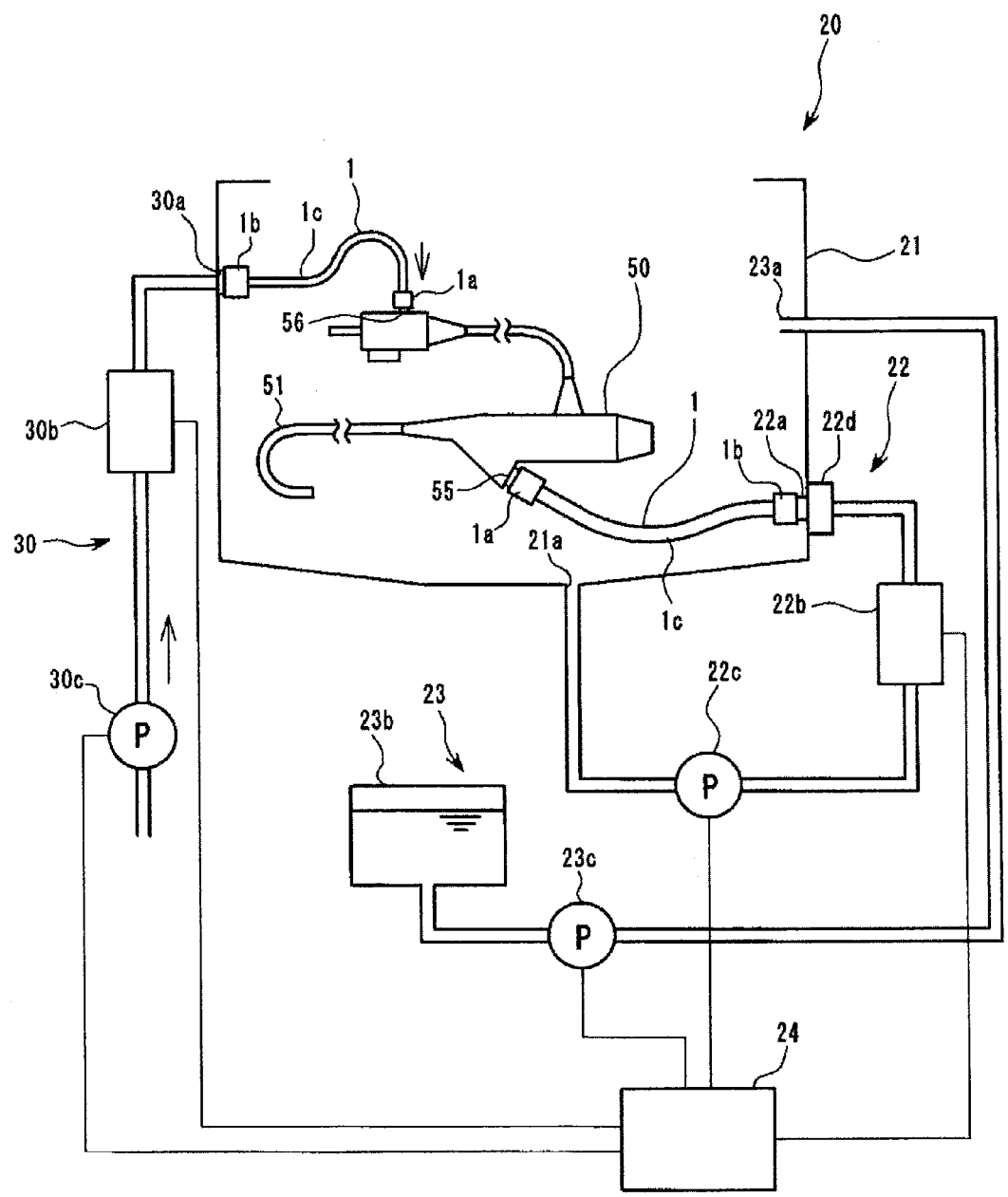
FIG. 12 is a view showing a configuration of a fluid delivery apparatus of a third embodiment.

As shown in FIG. 12, in the present embodiment, the fluid delivery apparatus 20 further includes a gas delivery section 30 that delivers gas, and the endoscope connection tool 1 connects the gas delivery section 30 which delivers gas and a pipe sleeve 56 which is provided in the endoscope 50.

The pipe sleeve 56 has an opening portion for feeding gas into an internal space of the endoscope 50 when a water leakage test of the endoscope 50 is performed. The water leakage test is a test that confirms that holes are not generated in an outer sheath and a conduit wall for keeping the inside of the endoscope 50 hermetic. In the water leakage test, gas is fed into the internal space of the endoscope 50 from the pipe sleeve 56, and presence or absence of leakage of the gas is checked. Presence or absence of leakage of the gas from the internal space of the endoscope 50 can be confirmed by a method for measuring atmospheric pressure, and a method for visually recognizing presence or absence of generation of air bubbles in a periphery of the endoscope 50 which is submerged in water.

The gas delivery section 30 includes a delivery port 30a, a flow rate detection portion 30b and a pump 30c. The gas delivery section 30 delivers gas such as air with a predetermined pressure from the delivery port 30a. The delivery port 30a is connected to the pipe sleeve 56 of the endoscope 50 via the endoscope connection tool 1. The gas which is delivered from the delivery port 22a passes through the endoscope connection tool 1 and the pipe sleeve 56, and is delivered into the internal space of the endoscope 50.

The flow rate detection portion 30b is a device that detects a flow rate of the gas which is discharged from the delivery port 30a. The control section 24 determines that the endoscope connection tool 1 is detached from the pipe sleeve 55 when the flow rate of the fluid which is discharged from the delivery port 30a is larger than a threshold value that is set.

The configuration of the endoscope connection tool 1 is the same as the configurations described in the first and second embodiments. Accordingly, in the present embodiment, a difference between the flow rate Q1 of the gas which is delivered from the delivery port 30a when the pipe sleeve joint 1a is correctly fitted to the pipe sleeve 55 and the flow rate Q2 of the gas which is delivered from the delivery port 30a when the pipe sleeve joint 1a is detached from the pipe sleeve 55 can be also clarified. Consequently, the control section 24 can correctly determine whether or not the endoscope connection tool 1 is detached from the pipe sleeve 56 based on the flow rate of the gas which is discharged from the delivery port 30a.

Note that the present invention is not limited to the aforementioned embodiments, and can be properly modified within the range without departing from the gist or the idea of the invention that can be read from claims and the entire description, and the endoscope connection tool accompanied by such modifications is also included in the technical range of the present invention.

What is claimed is:

1. An endoscope connection tool, comprising:
    a cylindrical portion having an inflow port to which a fluid delivery apparatus is connected, a discharge port from which a fluid that flows in from the inflow port is discharged, and a flow path that connects the inflow port and the discharge port;
    a detection hole that is opened in an outer periphery of the cylindrical portion, and communicates with the flow path;
    a holding portion that engages with a pipe sleeve of an endoscope, and thereby holds the discharge port in a position facing an opening portion of the pipe sleeve;
    a cover portion including
        a lid portion that is placed at the outer periphery of the cylindrical portion, moves to advance and retreat between a first position along the flow path and a second position which is nearer to the inflow port than the first position, the lid portion opening the detection hole when the lid portion is at the first position, the lid portion closing or narrowing the detection hole when the lid portion is at the second position, and
        a protruded portion that, when the holding portion is engaged with the pipe sleeve, abuts on an outer surface of the endoscope to move the lid portion to the second position; and
    an urging member that is placed at the outer periphery of the cylindrical portion, extends and contracts in a direction along the flow path, and urges the lid portion in a direction from the second position to the first position.

2. The endoscope connection tool according to claim 1, wherein the urging member is a spring that connects the cylindrical portion and the cover portion.

* * * * *